(12) United States Patent
Keene et al.

(10) Patent No.: US 9,198,893 B2
(45) Date of Patent: Dec. 1, 2015

(54) COMBINATION ANTITUMOR THERAPY

(75) Inventors: Jeffery L. Keene, St. Louis, MO (US);
Dennis P. Riley, St. Louis, MO (US);
Robert A. Beardsley, University City, MO (US)

(73) Assignee: GALERA LABS, LLC, St. Louis, MO (US)

( * ) Notice: Subject to any disclaimer, the term of this patent is extended or adjusted under 35 U.S.C. 154(b) by 394 days.

(21) Appl. No.: 12/993,140

(22) PCT Filed: May 22, 2009

(86) PCT No.: PCT/US2009/045029
§ 371 (c)(1),
(2), (4) Date: Dec. 9, 2010

(87) PCT Pub. No.: WO2009/143454
PCT Pub. Date: Nov. 26, 2009

(65) Prior Publication Data
US 2011/0136756 A1    Jun. 9, 2011

Related U.S. Application Data

(60) Provisional application No. 61/055,418, filed on May 22, 2008.

(51) Int. Cl.
| | |
|---|---|
| *A01N 55/02* | (2006.01) |
| *A61K 31/28* | (2006.01) |
| *A61K 31/337* | (2006.01) |
| *A61K 45/06* | (2006.01) |
| *A61K 31/555* | (2006.01) |

(52) U.S. Cl.
CPC .............. *A61K 31/28* (2013.01); *A61K 31/337* (2013.01); *A61K 31/555* (2013.01); *A61K 45/06* (2013.01)

(58) Field of Classification Search
CPC ..... A61K 31/28; A61K 31/337; A61K 31/47; A61K 45/06; A61K 2300/00; A61K 31/7052
See application file for complete search history.

(56) References Cited

U.S. PATENT DOCUMENTS 5,637,578 A * 6/1997 Riley et al. ................... 514/186

FOREIGN PATENT DOCUMENTS

WO    WO 2005/060976 A2 * 7/2005 ............ A61K 31/675

OTHER PUBLICATIONS

Alexandre, J., Nicco, C., Chéreau, C., Laurent, A., Weill, B., Goldwasser, F., Batteux, F. (2006) Journal of National Cancer Institute, vol. 98, p. 236-244.*
Machine translation of WO 2005/060976 A2 by Microsoft (2005) [online] [Retrieved Jan. 23, 2013] Retrieved from the internet <http://patentscope.wipo.int/search/en/structuredSearch.jsf>.*
Salvemini, D., Riley, D.P. (2000) Nonpeptidyl mimetics of superoxide dismutase in clinical therapies for diseases. Cellular and Molecular Life Sciences, vol. 57, p. 1489-1492.*
Ansel, H.C., Allen, Jr., L.V., Popovich, N.G. (1999) Pharmaceutical Dosage Forms and Drug Delivery Systems. Published by Lippincott Williams & Wilkins, p. 48-53.*
GEMZAR® product sheet (1996). Published by Eli Lilly and Company.*
Rocklage, S.M., Cacheris, W.P., Quay, S.C., Hahn, F.E., Raymond, K.N. (1989) Manganese (II) N,N'-Dipyridoxylethylenediamine-N,N'-diacetate 5,5'-Bis(phosphate). Synthesis and Characterization of a Paramagnetic Chelate for Magnetic Resonance Imanging Enhancement. Inorganic Chemistry, vol. 28, p. 477-485.*
Wagner, B. A., et al., Myeloperoxidase is involved in H2O2-induced apoptosis of HL-60 human leukemia cells, J. Biol. Chem, 2000, 272(29), 22461-9 Jul. 21, 2000.
Chen, Q., et al., Pharmacologic ascorbic acid concentrations selectively kill cancer cells: action as a pro-drug to deliver hydrogen peroxide to tissues, PNAS, 2005, 102(38), 13604-9 Sep. 20, 2005.
Rodriguez, et al., Mitochondrial or cytosolic catalase reverses the MnSOD-dependent inhibition of proliferation by enhancing respiratory chain activity, net ATP production, and decreasing the steady state levels of H2O2, Free Rad. Bio. & Med May 26, 2000.
Alexandre, J., et al., Novel Action of Paclitaxel against Cancer Cells: Bystander Effect Mediated by Reactive Oxygen Species, Cancer Research, 2007, 67(8), 3512-3517 Apr. 17, 2007.
Muscoli, C., et al., On the selectivity of superoxide dismutase mimetics and its importance in pharmacological studies, British Journal of Pharmacology, 2003, 140(3), 445-460 Oct. 1, 2003.
Sawyer, D. T. et al., How super is superoxide?, Acc. Chem. Res., 1981, 14, 393-400 Mar. 12, 1981.
Li, S., et al., The Role of Cellular Glutathione Peroxidase Redox Regulation in the Suppression of Tumor Cell Growth by Manganese Superoxide Dismutase, Cancer Res., 2000, 60(14), 3927-3939 Jul. 15, 2000.
Buettner, G. R., et al., A New Paradigm: Manganese Superoxide Dismutase Influences the Production of H2O2 in Cells and Thereby Their Biological State, Free Radical Biology and Medicine, 2006, 41(8), 1338-50 Oct. 15, 2006.
L.W. Oberley, "Mechanism of the tumor suppressive effect of MnSOD overexpression", Biomedicine & Pharmacotherapy, 59, 143-48 (2005).

* cited by examiner

*Primary Examiner* — Scarlett Goon
(74) *Attorney, Agent, or Firm* — Bryan Cave LLP

(57) ABSTRACT

The present disclosure relates to methods of treating cancers that are responsive to antimetabolite or antimitotic anti-cancer agents. The methods involve the use of at least one anti-cancer agent selected from antimetabolite anti-cancer agents, antimitotic anti-cancer agents, and combinations thereof, and a superoxide dismutase mimetic to potentiate the therapeutic effect of the anti cancer agent(s).

22 Claims, 2 Drawing Sheets

Human A549 non-small cell lung carcinoma (NSCLC) cells were implanted in the flank of mice. Dosing of test articles or vehicle was initiated on day 9 according to the following schedule.

| Treatment | Dose | Route | Schedule |
|---|---|---|---|
| KM4419 | 30 mpk | IP | BID d9-23 |
| Paclitaxel | 12.5 mpk | IP | QD d9-13 |

COMBINATION ANTITUMOR THERAPY

CROSS-REFERENCE TO RELATED APPLICATIONS

This application is a 371 National based on International Application No. PCT/US2009/045029, filed on May 22, 2009, which claims priority to U.S. Provisional Application No. 61/055,418, filed May 22, 2008. Each of these applications is incorporated by reference herein in its entirety.

TECHNICAL FIELD

The present disclosure relates to the field of antitumor treatment. More specifically, it relates to cancer therapies that produce synergistic or additive effects when mimetics of superoxide dismutase and certain anti-cancer agents are administered in combination.

BACKGROUND

It is known that at least some tumor cells are deficient in superoxide dismutase (SOD) activity, and SOD mimetics have been suggested in treating metastases. See, for example, Simic, M. G., et al., "Oxygen Radicals in Biology and Medicine," *Basic Life Sciences*, Vol. 49, Plenum Press, N.Y. and London (1988); Weiss, J. Cell. Biochem. (1991) Suppl. 15C, 216 Abstract C110; Petkau, A., Cancer Treat. Rev. (1986) 13:17-44; McCord, J. M., J. Free Rad. Biol. Med. (1986) 2:307-310; and Bannister, J. V., et al., Crit. Rev. Biochem. (1987) 22:111-180.

In addition, a wide variety of chemotherapeutic agents are known, and the effects of the chemotherapeutic agents described herein have been disclosed. For example, it is known that gemcitabine is incorporated into RNA and DNA of tumor cell lines and that it is active against murine colon tumors, among others (see, e.g., Ruiz van Haperen, V. W., et al., Biochem. Pharmacol. (1993) 46:762-766 and Veerman, G., et al., Cancer Chemother. Pharmacol. (1996) 38:335-342). Combination treatment using gemcitabine with Imatinib mesylate enhances the therapeutic effects in human malignant mesothelioma xenografts, as described by Bertino, P., et al., Clin. Cancer Res. (2008) 14:541-548.

Various superoxide dismutase mimetics are also known in the art. For example, manganese and iron complexes of pentaazacyclopentadecane ligands are described in U.S. Pat. Nos. 5,610,293; 5,637,578 and 5,874,421, among others. These patents indicate that these particular superoxide dismutase mimetics are useful in treating metastases.

In addition, it has been reported that combination treatments of the superoxide dismutase mimetic KM4403 with interleukin-2 (IL-2) potentiates the antitumor effect of IL-2. See, Samlowski, W. E., et al., Nature Medicine (2003) 9:750-755.

SUMMARY OF THE DISCLOSURE

Among the various aspects of the present invention may be noted the discovery that treatment with superoxide dismutase mimetics and with certain anti-cancer, antineoplastic, or chemotherapeutic agents can effectively be combined to result in enhanced treatment of cancers, in particular solid tumors. These combinations have been demonstrated to slow the growth of solid tumors and to delay any regrowth.

Briefly, therefore, the present invention is directed to a method of treating a cancer that is responsive to an antimetabolite or antimitotic anti-cancer agent in a mammalian subject. The method comprises administering to the subject at least one anti-cancer agent selected from antimetabolite anti-cancer agents, antimitotic anti-cancer agents, and combinations thereof, and a selective superoxide dismutase mimetic to potentiate the therapeutic effect of the anti-cancer agent(s) wherein the selective superoxide dismutase mimetic has no significant activity toward hydrogen peroxide.

Other objects and features will be in part apparent and in part pointed out hereinafter.

DETAILED DESCRIPTION

Figure 1:
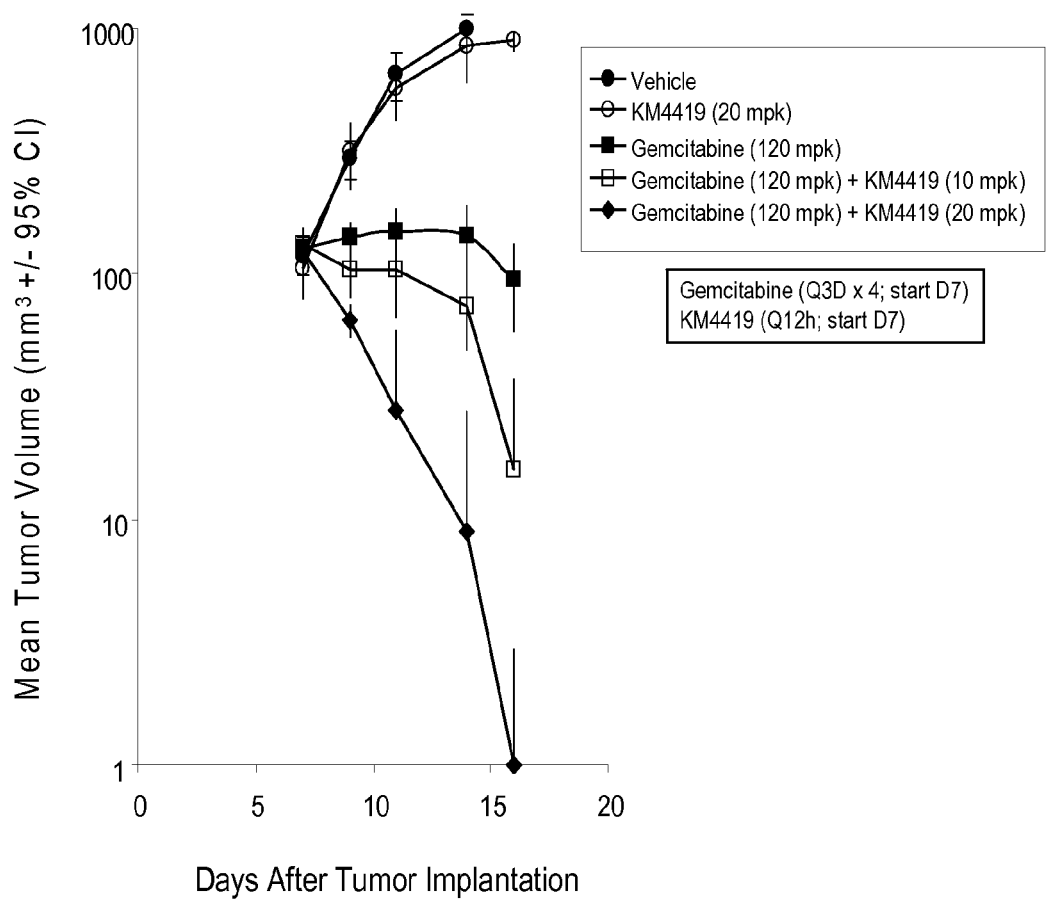
FIG. 1 is a graph that shows the effect of the combination of the SOD mimetic KM4419 with gemcitabine in a mouse model of tumor growth.

The present disclosure is generally directed to methods and pharmaceutical compositions for the treatment of cancers, and particularly cancers that are responsive to antimetabolite or antimitotic anti-cancer agents. The methods described herein involve the administration of at least one anti-cancer agent(s) selected from antimetabolite anti-cancer agents, antimitotic anti-cancer agents, and combinations thereof, and a superoxide dismutase mimetic. In particular, the superoxide dismutase mimetic is preferably used in combination with an antimetabolite agent, an antimitotic agent, or both an antimetabolite agent and an antimitotic agent. In one embodiment, for example, a superoxide dismutase mimetic is used in combination with an antimetabolite agent. In another embodiment, a superoxide dismutase mimetic is used in combination with an antimitotic agent. In yet another embodiment, a superoxide dismutase mimetic, an antimetabolite, and an antimitotic agent are used in combination. In accordance with the methods described herein, the superoxide dismutase mimetic compound and the antimetabolite and/or antimitotic agent are administered in combination; that is, they can be administered simultaneously (concurrently), or sequentially. In certain embodiments, the anti-cancer agent(s) and the superoxide dismutase mimetic are administered in the absence of the administration of a non-superoxide dismutase mimetic radical scavenger which reduces superoxide levels without creating hydrogen peroxide and/or reducing hydrogen peroxide levels in the treated cells. Pharmaceutical compositions including a superoxide dismutase mimetic, in combination with an antimetabolite agent and/or an antimitotic agent, and a pharmaceutically acceptable excipient, are also described herein.

Without being bound to any particular theory, the present disclosure relates, in part, to the discovery that the co-administration of the anti-cancer agents described herein (e.g., antimetabolite agents and/or antimitotic agents) and a superoxide dismutase mimetic potentiates the therapeutic effect of the anti-cancer agents. Potentiation of the therapeutic effect of the anti-cancer agents may involve enhancement of the cytotoxic effect of the anti-cancer agent generally, or may involve enhancement of the various mechanisms of action of the anti-cancer agent, individually or collectively; regardless of the actual mechanism, however, in a preferred embodiment, the combined effect of the anti-cancer agent(s) and the superoxide dismutase mimetic is greater than the sum of the effects produced by any of these agents alone (i.e., the effect is greater than additive).

It is generally known that superoxide dismutase mimetics may be used, per se, as anticancer agents (see, e.g., Simic, M. G., et al., supra; Weiss, supra; Petkau, A., supra, etc.). Superoxide, or enzymes responsible for its production, can be overexpressed in cancer cells, while native superoxide dismutase production can be inhibited by the tumor cells, leading to superoxide accumulation. Superoxide dismutase mimetics can take the place of native superoxide dismutase and catalyze the conversion of superoxide to hydrogen peroxide, which is helpful in killing the tumor cells. As described in further detail below, in certain embodiments the superoxide dismutase mimetic can be administered to increase the capacity of the cells to dismute superoxide. Thereafter, anti-cancer agent(s) such as antimetabolite agents, antimitotic agents, and combinations thereof can be administered.

In accordance with one aspect of the present invention and based upon evidence obtained to-date, the effect of the anticancer agents and/or the superoxide dismutase mimetic may be enhanced by reducing the ability of the tumor cell to rid itself of the hydrogen peroxide product of the dismuted superoxide; this reduction may be accomplished through the use of an antimetabolite anti-cancer agent. Antimetabolite agents interfere with DNA production and the corresponding synthesis of two enzyme families, catalase and glutathione peroxidase, which, among other things, degrade hydrogen peroxide to water and oxygen. These particular enzymes have relatively high turnover rates, and inhibiting their synthesis limits the ability of the tumor cell to rid itself of hydrogen peroxide. Without being bound to any particular theory, and based upon evidence obtained to-date, it is presently believed that when the superoxide dismutase mimetic is combined with the antimetabolite agent, for instance, cytotoxic effects are enhanced due to the downregulation of the hydrogen peroxide-digesting enzymes by the antimetabolite agent, and the corresponding diminished ability of the cell to remove cytotoxic hydrogen peroxide produced by the superoxide dismutase mimetic. Regardless of the mechanism, the result of the combined treatment is enhanced cytotoxicity and tumor killing.

Antimitotic compounds, on the other hand, stabilize or inhibit tubulin production, which directly or indirectly generates reactive oxygen species such as superoxide. Without being bound to any particular theory, and based upon evidence obtained to-date, it is presently believed that when superoxide dismutase mimetics are used in combination with antimitotic agents, there is an increased superoxide supply for the superoxide dismutase mimetic to convert to toxic hydrogen peroxide. Regardless of the mechanism, the result of the combined treatment is enhanced cytotoxicity and tumor killing.

When the superoxide dismutase mimetic, antimetabolite agent, and antimitotic agent are used in combination, further benefits may be derived. Without being bound to any particular theory, and based upon evidence obtained to-date, it is presently believed that not only is there an increased supply of superoxide as a result of the action of the antimitotic agent and a corresponding increase in the conversion of superoxide to hydrogen peroxide by the superoxide dismutase mimetic, the hydrogen peroxide product can accumulate and exert its toxic effect for a longer period of time because the enzymes that normally catalyze its conversion to water and oxygen have been downregulated or inhibited by the antimetabolite agent. It is further believed, as a result, that the therapeutic or cytotoxic effect of the various compounds are potentiated by reducing the ability of the tumor cells to remove the hydrogen peroxide product through use of the antimetabolite agent, while the superoxide supply is increased by the action of the antimitotic agent, which in turn leads to increased production of toxic hydrogen peroxide by the superoxide dismutase mimetic. Regardless of the mechanism, the result of the combined treatment is enhanced cytotoxicity and tumor cell killing.

Anti-Cancer Agent(s)

As noted herein, the methods of the present disclosure involve the administration of at least one anti-cancer agent selected from antimetabolite anti-cancer agents and antimitotic anti-cancer agents, and combinations thereof, to a subject. Various antimetabolite and antimitotic anti-cancer agents may be employed in the methods and compositions described herein.

Antimetabolite Agents

In certain embodiments, the compositions and methods described herein involve the use of a superoxide dismutase mimetic in combination with an antimetabolite agent, and optionally further in combination with an antimitotic agent. In general, a range of antimetabolite agents may be employed in the compositions and methods of the disclosure, which are known to those of skill in the art.

Antimetabolic anti-cancer agents typically structurally resemble natural metabolites, which are involved in normal metabolic processes of cancer cells such as the synthesis of nucleic acids and proteins. The antimetabolites, however, differ enough from the natural metabolites such that they interfere with the metabolic processes of cancer cells. In the cell, antimetabolites are mistaken for the metabolites they resemble, and are processed by the cell in a manner analogous to the normal compounds. The presence of the "decoy" metabolites prevents the cells from carrying out vital functions and the cells are unable to grow and survive. For example, antimetabolites may exert cytotoxic activity by substituting these fraudulent nucleotides into cellular DNA, thereby disrupting cellular division, or by inhibition of critical cellular enzymes, which prevents replication of DNA.

In one embodiment, therefore, the antimetabolite anti-cancer agent is a nucleotide or a nucleotide analog. In certain embodiments, for example, the antimetabolite agent may comprise purine (e.g., guanine or adenosine) or analogs thereof, or pyrimidine (cytidine or thymidine) or analogs thereof, with or without an attached sugar moiety.

Suitable antimetabolite anti-cancer agents for use in the present disclosure may be generally classified according to the metabolic process they affect, and can include, but are not limited to, analogues and derivatives of folic acid, pyrimidines, purines, and cytidine. Thus, in one embodiment, the antimetabolite agent(s) is selected from the group consisting of cytidine analogs, folic acid analogs, purine analogs, pyrimidine analogs, and combinations thereof.

In one particular embodiment, for example, the antimetabolite agent is a cytidine analog. According to this embodiment, for example, the cytidine analog may be selected from the group consisting of cytarabine (cytosine arabinodside), azacitidine (5-azacytidine), and salts, analogs, and derivatives thereof.

In another particular embodiment, for example, the antimetabolite agent is a folic acid analog. Folic acid analogs or antifolates generally function by inhibiting dihydrofolate reductase (DHFR), an enzyme involved in the formation of nucleotides; when this enzyme is blocked, nucleotides are not formed, disrupting DNA replication and cell division. According to certain embodiments, for example, the folic acid analog may be selected from the group consisting of denopterin, methotrexate (amethopterin), pemetrexed, pteropterin, raltitrexed, trimetrexate, and salts, analogs, and derivatives thereof.

In another particular embodiment, for example, the antimetabolite agent is a purine analog. Purine-based antimetabolite agents function by inhibiting DNA synthesis, for example, by interfering with the production of purine containing nucleotides, adenine and guanine which halts DNA synthesis and thereby cell division. Purine analogs can also be incorporated into the DNA molecule itself during DNA synthesis, which can interfere with cell division. According to certain embodiments, for example, the purine analog may be selected from the group consisting of acyclovir, allopurinol, 2-aminoadenosine, arabinosyl adenine (ara-A), azacitidine, azathiprine, 8-aza-adenosine, 8-fluoro-adenosine, 8-methoxy-adenosine, 8-oxo-adenosine, cladribine, deoxycoformycin, fludarabine, gancylovir, 8-aza-guanosine, 8-fluoro-guanosine, 8-methoxy-guanosine, 8-oxo-guanosine, guanosine diphosphate, guanosine diphosphate-beta-L-2-aminofucose, guanosine diphosphate-D-arabinose, guanosine diphosphate-2-fluorofucose, guanosine diphosphate fucose, mercaptopurine (6-MP), pentostatin, thiamiprine, thioguanine (6-TG), and salts, analogs, and derivatives thereof.

In yet another particular embodiment, for example, the antimetabolite agent is a pyrimidine analog. Similar to the purine analogs discussed above, pyrimidine-based antimetabolite agents block the synthesis of pyrimidine-containing nucleotides (cytosine and thymine in DNA; cytosine and uracil in RNA). By acting as "decoys," the pyrimidine-based compounds can prevent the production of nucleotides, and/or can be incorporated into a growing DNA chain and lead to its termination. According to certain embodiments, for example, the pyrimidine analog may be selected from the group consisting of ancitabine, azacitidine, 6-azauridine, bromouracil (e.g., 5-bromouracil), capecitabine, carmofur, chlorouracil (e.g. 5-chlorouracil), cytarabine (cytosine arabinoside), cytosine, dideoxyuridine, 3'-azido-3'-deoxythymidine, 3'-dideoxycytidin-2'-ene, 3'-deoxy-3'-deoxythymidin-2'-ene, dihydrouracil, doxifluridine, enocitabine, floxuridine, 5-fluorocytosine, 2-fluorodeoxycytidine, 3-fluoro-3'-deoxythymidine, fluorouracil (e.g., 5-fluorouracil (also known as 5-FU), gemcitabine, 5-methylcytosine, 5-propynylcytosine, 5-propynylthymine, 5-propynyluracil, thymine, uracil, uridine, and salts, analogs, and derivatives thereof. In one embodiment, the pyrimidine analog is other than 5-fluorouracil. In another embodiment, the pyrimidine analog is gemcitabine or a salt thereof.

In certain embodiments, the antimetabolite agent is selected from the group consisting of 5-fluorouracil, capecitabine, 6-mercaptopurine, methotrexate, gemcitabine, cytarabine, fludarabine, pemetrexed, and salts, analogs, derivatives, and combinations thereof. In other embodiments, the antimetabolite agent is selected from the group consisting of capecitabine, 6-mercaptopurine, methotrexate, gemcitabine, cytarabine, fludarabine, pemetrexed, and salts, analogs, derivatives, and combinations thereof. In one particular embodiment, the antimetabolite agent is other than 5-fluorouracil. In a particularly preferred embodiment, the antimetabolite agent is gemcitabine or a salt or thereof (e.g., gemcitabine HCl (Gemzar®)).

Other antimetabolite anti-cancer agents may be selected from, but are not limited to, the group consisting of acanthifolic acid, aminothiadiazole, brequinar sodium, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, Wellcome EHNA, Merck & Co. EX-015, fazarabine, fludarabine phosphate, N-(2'-furanidyl)-5-fluorouracil, Daiichi Seiyaku FO-152, 5-FU-fibrinogen, isopropyl pyrrolizine, Lilly LY-188011; Lilly LY-264618, methobenzaprim, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, tiazofurin, Erbamont TIF, tyrosine kinase inhibitors, Taiho UFT and uricytin, among others.

Antimitotic Agents

Compositions and methods described herein also involve the use of a superoxide dismutase mimetic in combination with an antimitotic anti-cancer agent, and optionally further in combination with an antimetabolite agent. In general, a range of antimetabolite agents may be employed in the compositions and methods of the disclosure, which are known to those of skill in the art.

In one embodiment, the antimitotic agent is a microtubule inhibitor or a mictrotubule stabilizer. In general, microtubule stabilizers, such as taxanes and epothilones, bind to the interior surface of the beta-microtubule chain and enhance microtubule assembly by promoting the nucleation and elongation phases of the polymerization reaction and by reducing the critical tubulin subunit concentration required for microtubules to assemble. Unlike mictrotubule inhibitors, such as the vinca alkaloids, which prevent microtubule assembly, the microtubule stabilizers, such as taxanes, decrease the lag time and dramatically shift the dynamic equilibrium between tubulin dimers and microtubule polymers towards polymerization. In one embodiment, therefore, the microtubule stabilizer is a taxane or an epothilone. In another embodiment, the microtubule inhibitor is a vinca alkaloid.

One element of the combination therapy described herein includes the use of a taxane or derivative or analog thereof. The taxane may be a naturally derived compound or a related form, or may be a chemically synthesized compound or a derivative thereof, with antineoplastic properties. The taxanes are a family of terpenes, including, but not limited to paclitaxel (Taxol®) and docetaxel (Taxotere®), which are derived primarily from the Pacific yew tree, *Taxus brevifolia*, and which have activity against certain tumors, particularly breast and ovarian tumors. In one embodiment, the taxane is docetaxel or paclitaxel. Paclitaxel is a preferred taxane and is considered an antimitotic agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions.

Also included are a variety of known taxane derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; deoxygenated paclitaxel compounds such as those described in U.S. Pat. No. 5,440,056; and taxol derivatives described in U.S. Pat. No. 5,415,869. As noted above, it further includes prodrugs of paclitaxel including, but not limited to, those described in WO 98/58927; WO 98/13059; and U.S. Pat. No. 5,824,701. The taxane may also be a taxane conjugate such as, for example, paclitaxel-PEG, paclitaxel-dextran, paclitaxel-xylose, docetaxel-PEG, docetaxel-dextran, docetaxel-xylose, and the like. Other derivatives are mentioned in "Synthesis and Anticancer Activity of Taxol Derivatives," D. G. I. Kingston et al., Studies in Organic Chemistry, vol. 26, entitled "New Trends in Natural Products Chemistry" (1986), Attaur-Rabman, P. W. le Quesne, Eds. (Elsevier, Amsterdam 1986), among other references. Each of these references is hereby incorporated by reference herein in its entirety.

Various taxanes may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267) (each of which is hereby incorporated by reference herein in its entirety), or obtained from a variety of commercial sources, including for example, Sigma-Aldrich Co., St. Louis, Mo.

Alternatively, the antimitotic agent can be a microtubule inhibitor; in one preferred embodiment, the microtubule inhibitor is a vinca alkaloid. In general, the vinca alkaloids are mitotic spindle poisons. The vinca alkaloid agents act during mitosis when chromosomes are split and begin to migrate along the tubules of the mitosis spindle towards one of its poles, prior to cell separation. Under the action of these spindle poisons, the spindle becomes disorganized by the dispersion of chromosomes during mitosis, affecting cellular reproduction. According to certain embodiments, for example, the vinca alkaloid is selected from the group consisting of vinblastine, vincristine, vindesine, vinorelbine, and salts, analogs, and derivatives thereof.

The antimitotic agent can also be an epothilone. In general, members of the epothilone class of compounds stabilize microtubule function according to mechanisms similar to those of the taxanes. Epothilones can also cause cell cycle arrest at the G2-M transition phase, leading to cytotoxicity and eventually apoptosis. Suitable epithiolones include epothilone A, epothilone B, epothilone C, epothilone D, epothilone E, and epothilone F, and salts, analogs, and derivatives thereof. One particular epothilone analog is an epothilone B analog, ixabepilone (Ixempra™).

In certain embodiments, the antimitotic anti-cancer agent is selected from the group consisting of taxanes, epothilones, vinca alkaloids, and salts and combinations thereof. Thus, for example, in one embodiment the antimitotic agent is a taxane. More preferably in this embodiment the antimitotic agent is paclitaxel or docetaxel, still more preferably paclitaxel. In another embodiment, the antimitotic agent is an epothilone (e.g., an epothilone B analog). In another embodiment, the antimitotic agent is a vinca alkaloid.

Superoxide Dismutase Mimetics

As noted above, the present disclosure relates to combination therapies using superoxide dismutase mimetics which potentiate the therapeutic effect of at least one anti-cancer agent selected from antimetabolite agents, antimitotic agents, and combinations thereof. The superoxide dismutase mimetic component, a non-proteinaceous molecule that catalyzes the conversion of the superoxide radical, $O_2^-$, to molecular oxygen and hydrogen peroxide. In accordance with one embodiment, for example, the superoxide dismutase mimetic is administered to the subject to increase the capacity of the cancer cells to dismute superoxide.

Any superoxide dismutase mimetic capable of selectively catalyzing the conversion of superoxide to oxygen and hydrogen peroxide and exhibiting no significant activity toward hydrogen peroxide may be used in the methods, compositions, and formulations described herein.

Particularly preferred selective superoxide dismutase mimetics are those based on $Mn^{2+}$ and $Mn^{3+}$ complexes of pentaaza-macrocyclic ligands, such as those compositions disclosed in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041 (each of which is hereby incorporated herein by reference in its entirety). For example, selective superoxide dismutase mimetics such as those corresponding to Formulae (4403) and (4419) exhibit no detectable activity towards hydrogen peroxide, whereas non-selective superoxide dismutase mimetics such as mangafodipir, copper [II] diisopropylsalicylate (CuDIPS), manganese [III] tetrakis-(5,10,15,20)-benzoic acid porphyrin (MnTBAP), and the like, exhibit significant activity toward hydrogen peroxide. In general, the efficacy of the superoxide dismutase mimetic employed in the process of the present disclosure tends to decrease as the activity of the superoxide dismutase mimetic toward hydrogen peroxide increases. Accordingly, it is preferred that the ratio of the activity of the superoxide dismutase mimetic toward superoxide to the activity of the superoxide dismutase mimetic toward hydrogen peroxide be at least 10:1 (activity toward superoxide:activity toward hydrogen peroxide). More preferably, the ratio of the activity of the superoxide dismutase mimetic toward superoxide to the activity of the superoxide dismutase mimetic toward hydrogen peroxide is at least 100:1 (activity toward superoxide:activity toward hydrogen peroxide). Still more preferably, the ratio of the activity of the superoxide dismutase mimetic towards superoxide to the activity of the superoxide dismutase mimetic toward hydrogen peroxide is at least 1000:1 (activity toward superoxide:activity toward hydrogen peroxide). In one particularly preferred embodiment, the superoxide dismutase mimetic exhibits no detectable activity toward hydrogen peroxide.

In one embodiment, the superoxide dismutase mimetic corresponds to Formula (I):

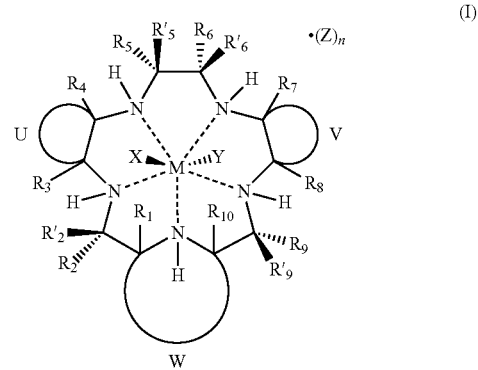

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands or charge-neutralizing anions which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, M.

As noted above in connection with the superoxide dismutase mimetic of Formula (I), M is $Mn^{2+}$ or $Mn^{3+}$. In one particular embodiment in which the superoxide dismutase mimetic corresponds to Formula (I), M is $Mn^{2+}$. In another particular embodiment in which the superoxide dismutase mimetic corresponds to Formula (I), M is $Mn^{3+}$.

In the embodiments in which one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are hydrocarbyl, for example, suitable hydrocarbyl moieties include, but are not limited to alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and aralkyl. In one embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, or heterocyclyl. More preferably in this embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl (e.g., $C_1$-$C_6$ alkyl, more typically $C_1$-$C_4$ alkyl). Thus, for example, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ may be independently hydrogen, methyl, ethyl, propyl, or butyl (straight, branched, or cyclic). In one preferred embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl.

In one preferred embodiment in which the superoxide dismutase mimetic corresponds to Formula (I), $R_1$, $R_2$, $R'_2$, $R_3$, $R_4$, $R_5$, $R'_5$, $R_7$, $R_8$, $R_9$, $R'_9$, and $R_{10}$ are each hydrogen and one of $R_6$ and $R'_6$ is hydrogen and the other of $R_6$ and $R'_6$ is methyl. In this embodiment, for example, $R_1$, $R_2$, $R'_2$, $R_3$, $R_4$, $R_5$, $R'_5$, $R_6$, $R_7$, $R_8$, $R_9$, $R'_9$, and $R_{10}$ may each be hydrogen while $R'_6$ is methyl. Alternatively, for example, $R_1$, $R_2$, $R'_2$, $R_3$, $R_4$, $R_5$, $R'_5$, $R'_6$, $R_7$, $R_8$, $R_9$, $R'_9$, and $R_{10}$ may each be hydrogen while $R_6$ is methyl. In another preferred embodiment in which the superoxide dismutase mimetic corresponds to Formula (I), $R_1$, $R_3$, $R_4$, $R_5$, $R'_5$, $R'_6$, $R_7$, $R_8$, and $R_{10}$ are each hydrogen, one of $R_2$ and $R'_2$ is hydrogen and the other of $R_2$ and $R'_2$ is methyl, and one of $R_9$ and $R'_9$ is hydrogen and the other of $R_9$ and $R'_9$ is methyl. In this embodiment, for example, $R_1$, $R'_2$, $R_3$, $R_4$, $R_5$, $R'_5$, $R_7$, $R_8$, $R_9$, and $R_{10}$ may each be hydrogen while $R_2$ and $R'_9$ are methyl. Alternatively, for example, $R_1$, $R_2$, $R_3$, $R_4$, $R_5$, $R'_5$, $R_7$, $R_8$, $R'_9$, and $R_{10}$ may each be hydrogen while $R'_2$ and $R_9$ are methyl. In another embodiment in which the superoxide dismutase mimetic corresponds to Formula (I), $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

In certain embodiments the U and V moieties are independently substituted or unsubstituted fused cycloalkyl moieties having 3 to 20 ring carbon atoms, more preferably 4 to 10 ring carbon atoms. In a particular embodiment, the U and V moieties are each trans-cyclohexanyl fused rings.

In certain embodiments the W moiety is a substituted or unsubstituted fused heteroaromatic moiety. In a particular embodiment, the W moiety is a substituted or unsubstituted fused pyridino moiety. Where W is a substituted fused pyridino moiety, for example, the W moiety is typically substituted with a hydrocarbyl or substituted hydrocarbyl moiety (e.g., alkyl, substituted alkyl) at the ring carbon atom positioned para to the nitrogen atom of the heterocycle. In a one preferred embodiment, the W moiety is an unsubstituted fused pyridino moiety.

As noted above, X and Y represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). For example, X and Y may be selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, among other possibilities. In one preferred embodiment, X and Y if present, are independently selected from the group consisting of halide, nitrate, and bicarbonate anions; more preferably in this embodiment, X and Y, if present, are halide anions; still more preferably chloro anions.

In the superoxide dismutase mimetic corresponding to Formula (I), Z is a counterion (e.g., a charge-neutralizing anion), wherein n is an integer from 0 to 3. In general, Z may correspond to counterions of the moieties recited above in connection for X and Y.

In combination, among certain preferred embodiments are superoxide dismutase mimetics corresponding to Formula (I) wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl;

U and V are each trans-cyclohexanyl fused rings;

W is a substituted or unsubstituted fused pyridino moiety; and

X, Y and Z are ligands or charge-neutralizing anions.

More preferably in these embodiments, M is $Mn^{2+}$; $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl; U and V are each trans-cyclohexanyl fused rings; W is an unsubstituted fused pyridino moiety; and X, Y, and Z, if present, are independently halide anions (e.g., fluoro, chloro, bromo, iodo).

In one preferred embodiment, the superoxide dismutase mimetic corresponds to Formula (II):

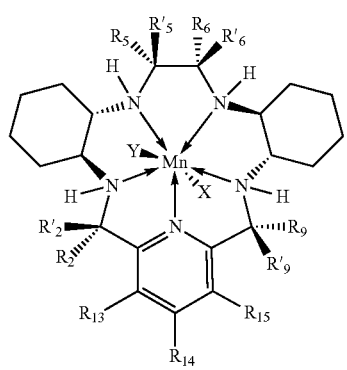

(II)

wherein $R_2$, $R'_2$, $R_5$, $R'_5$, $R_6$, $R'_6$, $R_9$, and $R'_9$ are independently hydrogen or lower alkyl;

$R_{13}$, $R_{14}$, and $R_{15}$ are independently halo, hydrogen, hydrocarbyl, substituted hydrocarbyl, acyl, acyloxy, ethers, thioethers, ligand moieties, and amino acid-containing moieties; and X and Y are ligands or charge-neutralizing anions.

In one embodiment, $R_5$, $R'_5$, $R_{13}$, $R_{14}$, and $R_{15}$ are each hydrogen. In accordance with this embodiment, for example, one of $R_2$ and $R'_2$ is hydrogen and the other of $R_2$ and $R'_2$ is methyl, or $R_2$ and $R'_2$ are each hydrogen; one of $R_6$ and $R'_6$ is hydrogen and the other of $R_6$ and $R'_6$ is methyl, or $R_6$ and $R'_6$ are each hydrogen; and one of $R_9$ and $R'_9$ is hydrogen and the other of $R_9$ and $R'_9$ is methyl, or $R_9$ and $R'_9$ are each hydrogen.

Where one or more of $R_{13}$, $R_{14}$, and $R_{15}$ are hydrocarbyl, for example, they may be independently alkyl, alkenyl, alkynyl, aryl, aralkyl, or alkaryl. Typically, such substituents contain from 1 to 20 carbon atoms (preferably 1 to 6 carbon atoms), and may be linear, branched, or cyclic. Where one or more of $R_{13}$, $R_{14}$, and $R_{15}$ are substituted hydrocarbyl, they may be independently substituted alkyl, substituted alkenyl, substituted alkynyl, substituted aryl, substituted aralkyl, or substituted alkaryl. These substituents may contain 1 to 20 carbon atoms (preferably 1 to 6 carbon atoms) and may be linear, branched, or cyclic; one or more hydrogen atoms of the substituted hydrocarbyl moieties, however, are replaced with a different substituent such as, for example, —OH, —OR, —COOH, —COOR, —CONH$_2$, —NH$_2$, —NHR, —NRR, —SH, —SR, —SO$_2$R, —SO$_2$H, —SOR, heterocyclo, and halo (including F, Cl, Br and I), among others, wherein each occurrence of R may be hydrocarbyl or substituted hydrocarbyl (e.g., substituted or unsubstituted alkyl, substituted or unsubstituted aryl, or substituted or unsubstituted aralkyl). One or more of $R_{13}$, $R_{14}$, and $R_{15}$ may be a ligand moiety, such as a targeting ligand (e.g., a polypeptide or protein-based ligand that is reactive with a particular compound, polypeptide or protein sequence, cell, cell surface receptor, antigen, and the like). In one embodiment, $R_{13}$ and $R_{15}$ are hydrogen and $R_{14}$ is halo, hydrogen, hydrocarbyl, substituted hydrocarbyl, acyl, acyloxy, ether, thioether, ligand, or amino acid-containing moiety. In another embodiment, $R_{13}$, $R_{14}$, and $R_{15}$ are each hydrogen.

Certain particularly preferred superoxide dismutase mimetic compounds for use in the methods and compositions described herein include those corresponding to Formulae (4444), (4459), (4401), (4462), (4403), and (4419):

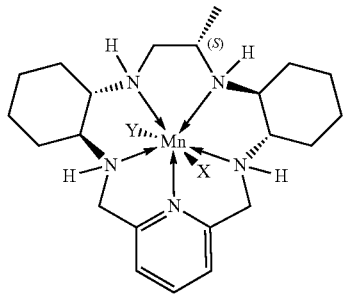

(4459)

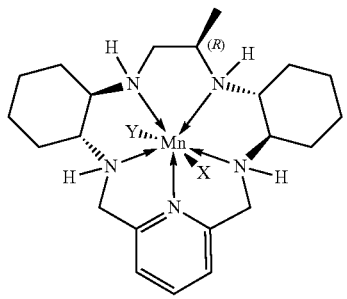

(4444)

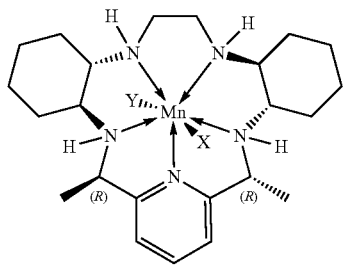

(4462)

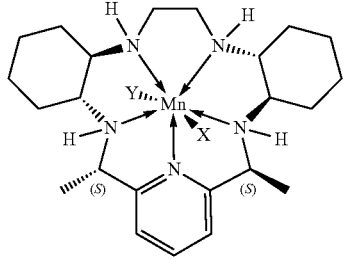

(4401)

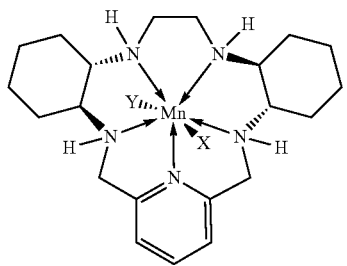

(4419)

-continued

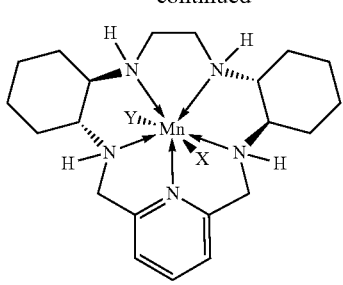
(4403)

wherein X and Y in each of Formulae (4444), (4459), (4401), (4462), (4403), and (4419) are independently ligands or charge-neutralizing anions. For example, in this embodiment, the superoxide dismutase mimetic compounds for use in the methods and compositions described herein include those corresponding to Formulae (4444), (4459), (4401), (4462), (4403), and (4419) with X and Y in each of these formulae being halide, more preferably chloro.

In a particularly preferred embodiment, the superoxide dismutase mimetic corresponds to Formula (KM4419) or Formula (KM4403):

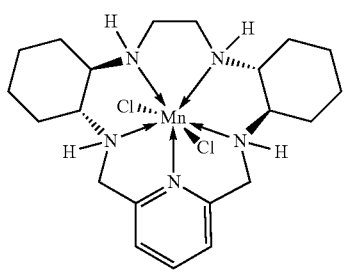
(KM4403)

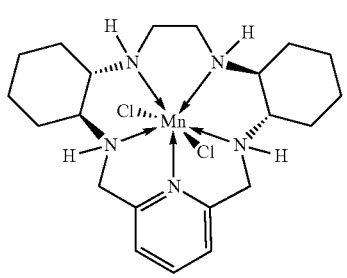
(KM4419)

Combination Therapies for Cancer

As noted above, one aspect of the present disclosure is directed to a method of treating cancer using a combination of treatment regimens. For example, such combinations may include, but are not limited to, the use of a selective superoxide dismutase mimetic and an antimetabolite agent, the use of a selective superoxide dismutase mimetic and an antimitotic agent, and the use of a selective superoxide dismutase mimetic, an antimetabolite agent, and an antimitotic agent, each of which is described in detail herein. The above combinations of selective superoxide dismutase mimetics, antimetabolite agents, and/or antimitotic agents are administered to a patient in combination; i.e., simultaneously (concurrently), or in sequence. In certain of these embodiments, the selective superoxide dismutase mimetics, antimetabolite agents, and/or antimitotic agents are administered in the absence of administration of a non-superoxide dismutase radical scavenger. Such radical scavengers may reduce the potentiating effects of the combinations described herein, and thus are generally disfavored.

The methods may also involve the use of additional pharmaceutical agents, including further antineoplastic chemotherapeutic agents, chemopreventative agents, and/or side-effect limiting agents, or other agents capable of treating cancer and/or alleviating the symptoms thereof, or still other agents capable of to treat other diseases and symptoms thereof. For example, the co-administration of the compounds described herein may be further used in conjunction with additional therapies known to those skilled in the art in the prevention or treatment of neoplasia, such as with radiation therapy, surgery, or with additional cytostatic or cytotoxic agents. The selective superoxide dismutase mimetic and the anti-cancer agent(s) are preferably unaccompanied by the administration of a non-superoxide dismutase mimetic composition having free radical or other reactive oxygen species (ROS) scavenger or decomposition catalyst activity in an amount that may decrease the therapeutic effect of the anti-cancer agent. Relative efficacy may be determined, for example, by use of an in vitro or in vivo model wherein the efficacy of a combination therapy that includes the composition (the non-superoxide dismutase mimetic having free radical or other ROS scavenger or decomposition catalyst activity) is compared to a combination that lacks such composition. The anti-cancer agent(s) and the superoxide dismutase mimetic are preferably administered in the absence of a non-superoxide dismutase mimetic having free radical or other ROS scavenger or decomposition catalyst activity, and in particular those non-superoxide dismutase mimetic compounds which reduce superoxide levels without creating hydrogen peroxide, and/or which reduce hydrogen peroxide levels. For instance, the anti-cancer agent(s) and the superoxide dismutase mimetic are preferably administered in the absence of amifostine, N-acetylcysteine, vitamin C, metalloporphyrins and related macrocycles, manganese(Salen) compounds, and the like. In one embodiment, for example, the anti-cancer agent(s) and the superoxide dismutase mimetic are administered in the absence of amifostine and N-acetylcysteine.

Co-therapy or combination therapy according to the methods described herein is intended to embrace administration of each compound in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent, or single or multiple parenteral administrations, or other routes of administration and dosage forms. When administered in combination, therefore, the therapeutic agents (i.e., the superoxide dismutase mimetic, the antimetabolite agent, and/or the antimitotic agent) can be formulated as separate compositions that are administered at the same time or sequentially at different times, or the therapeutic agents can be given as a single composition. Pharmaceutical compositions and formulations are discussed elsewhere herein.

It is not necessary that the superoxide dismutase mimetic(s), antimetabolite(s), and/or antimitotic(s), be administered simultaneously or essentially simultaneously; the agents and compounds may be administered in sequence. The advantage of a simultaneous or essentially simultaneous administration, or sequential administration, is well within the determination of the skilled clinician. For instance, while a pharmaceutical composition or formulation comprising a superoxide dismutase mimetic(s) may be advantageous for administering first in the combination for one particular treatment, prior administration of the antimetabolite and/or antimitotic agent(s) (or prior administration of the superoxide dismutase mimetic(s)) may be advantageous in another treatment. It is also understood that the instant combination of superoxide dismutase mimetics, antimetabolites, and antimitotics may be used in conjunction with other methods of treating cancer (typically cancerous tumors) including, but not limited to, radiation therapy and surgery, or other chemotherapy. It is further understood that a cytostatic or quiescent agent, or antiemetic agent, if any, may be administered sequentially or simultaneously with any or all of the other synergistic therapies.

Thus, the present disclosure encompasses a method for potentiating the therapeutic effects of anti-cancer agents, wherein a superoxide dismutase mimetic compound(s) and at least one anti-cancer agent selected from an antimetabolite agent(s), antimitotic agents, and combinations thereof, are administered simultaneously or sequentially. For instance, the present disclosure encompasses a method for the treatment of cancer wherein a superoxide dismutase mimetic compound(s) and an antimetabolite agent(s) are administered simultaneously or sequentially. By way of another example, the present disclosure encompasses a method for the treatment of cancer wherein a superoxide dismutase mimetic compound(s) and an antimitotic agent(s) are administered simultaneously or sequentially. Further, the present disclosure encompasses a method for the treatment of cancer wherein a superoxide dismutase mimetic compound(s), an antimetabolite agent(s), and an antimitotic agent(s) are administered simultaneously or sequentially.

As noted above, if the superoxide dismutase mimetic, antimetabolite agent, and antimitotic agent are not administered simultaneously or essentially simultaneously, then the initial order of administration of the components may be varied.

Thus, for example, a superoxide dismutase mimetic may be administered first, followed by the administration of an antimetabolite agent; or an antimetabolite agent may be administered first, followed by the administration of a superoxide dismutase mimetic. Similarly, a superoxide dismutase mimetic may be administered first, followed by the administration of an antimitotic agent; or an antimitotic agent may be administered first, followed by the administration of a superoxide dismutase mimetic. Where a superoxide dismutase mimetic, an antimetabolite agent, and an antimitotic agent are administered in sequence, the sequence may vary accordingly. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. By way of another example, an antimitotic agent may be administered initially (e.g., to increase superoxide production). The treatment is then continued with the administration of the superoxide dismutase mimetic (e.g., to convert the superoxide to hydrogen peroxide), optionally followed by administration of the antimetabolite (e.g., to retard hydrogen peroxide-degrading enzyme production), if desired, until the treatment protocol is complete. Other sequences of administration to exploit the potentiating effects described herein are contemplated.

In one preferred embodiment, the subject is pre-treated with the superoxide dismutase mimetic (i.e., the superoxide dismutase mimetic is pre-administered), followed by administration of the anti-cancer agent(s) (i.e., the antimetabolite(s) and/or the antimitotic(s)). In accordance with such embodiments, the anti-cancer agent(s) is/are is preferably administered at least 1 hour, but no more than 3 days, after administration of the superoxide dismutase mimetic. For example, in one embodiment, the anti-cancer agent(s) is/are administered between 1 hour and 2 days after administration of the superoxide dismutase mimetic. In another embodiment, for example, the anti-cancer agent(s) is/are administered between 1 hour and 1 day after administration of the superoxide dismutase mimetic. For example, the anti-cancer agent may be administered within 1 hour, 2 hours, 3 hours, 4 hours, 5 hours, 6 hours, 12 hours, 18 hours, 24 hours, 36 hours, or 48 hours after administration of the superoxide dismutase mimetic. In one particular embodiment, for example, the anti-cancer agent(s) is/are administered within 24 hours after administration of the superoxide dismutase mimetic. In these and other embodiments, the superoxide dismutase mimetic may be administered in multiple doses leading up to administration of the anti-cancer agent(s).

Alternatively, the subject may be pre-treated with the anti-cancer agent(s) (i.e., the antimetabolite(s) and/or the antimitotic(s)), followed by administration of the superoxide dismutase mimetic. In accordance with such embodiments, the superoxide dismutase mimetic is preferably administered within at least 1 plasma half-life of the anti-cancer agent(s), but no more than 4 plasma half-lives of the anti-cancer agent(s). For example, the superoxide dismutase mimetic may be administered within 1, 2, or 3 plasma half-lives of the anti-cancer agent(s).

In other alternative embodiments, the subject may be pre-treated with the superoxide dismutase mimetic, followed by administration of the anti-cancer agent(s), which is further followed by an additional administration of the superoxide dismutase mimetic. In accordance with this embodiment, for example, the standard superoxide dismutase mimetic dose may be separated into two (or more) portions, one portion of which is administered prior to administration of the anti-cancer agent(s), and the second portion of which is administered after administration of the anti-cancer agent(s). This staggered therapy regime could also be employed where the anti-cancer agent(s) is/are administered first. In addition, the subject could be pre-treated with a partial or full dose of superoxide dismutase mimetic, followed by administration of a first anti-cancer agent (e.g., one of the antimetabolite and the antimitotic), which is then followed by the administration of additional (or partial) dose of superoxide dismutase mimetic, which may be further followed by administration of a second anti-cancer agent (e.g., the other of the antimetabolite and the antimitotic).

As described in further detail below, the combinations of the disclosure may also be co-administered with other well known therapeutic agents that are selected for their particular usefulness against the condition that is being treated. Combinations may alternatively be used sequentially with known pharmaceutically acceptable agent(s) when a multiple combination formulation is inappropriate.

The superoxide dismutase mimetics, antimetabolite agents, and antimitotic agents are generally administered according to therapeutic protocols well known in the art. It will be apparent to those skilled in the art that the administration of the various components can be varied depending on the disease being treated and the known effects of superoxide dismutase mimetics, antimetabolite agents, and/or antimitotic agents on that disease. Also, in accordance with the knowledge of the skilled clinician, the therapeutic protocols (e.g., dosage amounts and times of administration) can be varied in view of the observed effects of the administered therapeutic agents (i.e., superoxide dismutase mimetics, antimetabolite agents, and/or antimitotic agents) on the patient, and in view of the observed responses of the disease to the administered therapeutic agents.

Also, in general, the superoxide dismutase mimetic(s), antimetabolite agent(s), and/or antimitotic agent(s) do not have to be administered in the same pharmaceutical composition, and may, because of different physical and chemical characteristics, have to be administered by different routes. For example, the superoxide dismutase mimetic may be administered orally to generate and maintain good blood levels thereof, while the antimetabolite agent and/or the antimitotic agent may be administered intravenously, or vice versa. The determination of the mode of administration and the advisability of administration, where possible, in the same pharmaceutical composition, or in separate pharmaceutical compositions (e.g., two or three separate compositions) is well within the knowledge of the skilled clinician. The initial administration can be made according to established protocols known in the art, and then, based upon the observed effects, the dosage, modes of administration and times of administration can be modified by the skilled clinician.

The particular choice of superoxide dismutase mimetics, antimetabolite agents, and antimitotic agents (each of which are described in detail herein), and other related therapies (such as surgery or radiation), will depend upon the diagnosis of the attending physicians and their judgment of the condition of the patient and the appropriate treatment protocol.

Thus, in accordance with experience and knowledge, the practicing physician can modify each protocol for the administration of a component (superoxide dismutase mimetics, antimetabolites, and/or antimitotics) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The products of which the combination are composed may be administered simultaneously, separately or spaced out over a period of time so as to obtain the maximum efficacy of the combination; it being possible for each administration to vary in its duration from a rapid administration to a relatively continuous perfusion of either component (in separate formulations or in a single formulation). As a result, for the purposes of the present disclosure, the combinations are not exclusively limited to those which are obtained by physical association of the constituents, but also to those which permit a separate administration, which can be simultaneous or spaced out over a period of time.

Accordingly, administration of the components described herein can occur as a single event or over a time course of treatment. For example, one or more of the superoxide dismutase mimetics, antimetabolites, and/or antimitotics can be administered (simultaneously or in sequence) hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the patient in need of such treatment. Alternatively, the compounds and agents can be administered hourly, daily, weekly, bi-weekly, or monthly, for a period of several weeks, months, years, or over the lifetime of the patient as a prophylactic measure.

The dose or amount of pharmaceutical compositions including the superoxide dismutase mimetics, antimetabolites, and/or antimitotics administered to the patient should be an effective amount for the intended purpose, i.e., treatment or prophylaxis of one or more of the diseases, pathological disorders, and medical conditions discussed herein, particularly cancer. Generally speaking, the effective amount of the composition administered can vary according to a variety of factors such as, for example, the age, weight, sex, diet, route of administration, and the medical condition of the patient in need of the treatment. Specifically preferred doses are discussed more fully below. It will be understood, however, that the total daily usage of the compositions described herein will be decided by the attending physician or veterinarian within the scope of sound medical judgment.

As noted above, the combinations can be co-administered (via a co-formulated dosage form or in separate dosage forms administered at about the same time). The combinations can also be administered separately, at different times, with each agent in a separate unit dosage form. Numerous approaches for administering anti-cancer drugs and superoxide dismutase mimetics are known in the art, and can readily be adapted for use in the present disclosure. The pharmaceutical compositions may be delivered orally, e.g., in a tablet or capsule unit dosage form, or parenterally, e.g., in an injectable unit dosage form, or by some other route. For systemic administration, for example, the drugs can be administered by, for example, intravenous infusion (continuous or bolus). The compositions can be used for any therapeutic or prophylactic treatment where the patient benefits from treatment with the combination.

The specific therapeutically effective dose level for any particular patient will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. For example, it is well within the skill of the art to start doses of the compound(s) at levels lower than those required to achieve the desired therapeutic effect and to gradually increase the dosage until the desired effect is achieved. If desired, the effective daily doses may be divided into multiple doses for purposes of administration. Consequently, single dose compositions may contain such amounts or submultiples to make up the daily dose.

Appropriate scheduling and dosing of such administration can readily be determined by those of skill in this art based on, for example, preclinical studies in animals and clinical studies (e.g., phase I studies) in humans. In addition, analysis of treatment using similar drugs, as well as monitoring factors such as blood counts (e.g., neutrophil and platelet counts) and vital signs in patients can be used, as is well understood in the art. Many regimens used to administer chemotherapeutic drugs involve, for example, intravenous administration of a drug (or drugs) followed by repetition of this treatment after a period (e.g., 1-4 weeks) during which the patient recovers from any adverse side effects of the treatment.

Suitable or preferred doses for each of the components employed in the methods or included in the compositions described herein are generally known in the art. Preferred dosages for gemcitabine, for instance, are within the range of 80-1500 mg/m² of body surface area, typically 500-1300 mg/m² of body surface area, administered weekly. A typical dose of a superoxide dismutase mimetic, for example, can be in the range of 1.0-500 mg/m² of body surface area, typically 10-250 mg/m² of body surface area, administered daily. For taxanes, suitable doses range from about 20-500 mg/m² of body surface area, typically 60-350 mg/m² of body surface area. However, the dosage may vary depending on the dosing schedule, which can be adjusted as necessary to achieve the desired therapeutic effect. It should be noted that the ranges of effective doses provided herein are not intended to limit the disclosure and represent exemplary dose ranges. The most preferred dosage will be tailored to the individual subject, taking into account, among other things, the particular combinations employed, and the patient's age, sex, weight, physical condition, diet, etc., as is understood and determinable by one of ordinary skill in the art without undue experimentation.

The chemotherapy doses used are typically just below the maximal tolerated dose and therefore dose limiting toxicities generally include, nausea, vomiting, diarrhea, hair loss, neutropenia and the like.

Further, as is well known in the art, treatment using the methods of the invention can be carried out in conjunction with the administration of antiemetics, which are drugs that are used to reduce the nausea and vomiting that are common side effects of cancer chemotherapy. Examples of such drugs include major tranquilizers (e.g., phenothiazines, such as chlorpromazine and prochlorperazine), dopamine antagonists (e.g., metoclopramide), serotonin antagonists (e.g., ondansetron and granisetron), cannabinoids (e.g., dronabinol), and benzodiazepine sedatives.

Methods for the safe and effective administration of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is hereby incorporated by reference herein.

Treatment of cancer, or cancer therapies, described herein includes achieving a therapeutic benefit and/or a prophylactic benefit. Therapeutic benefits generally refer to at least a partial eradication or amelioration of the underlying disorder being treated. For example, in a cancer patient, therapeutic benefit includes (partial or complete) eradication or amelioration of the underlying cancer. Also, a therapeutic benefit is achieved with at least partial, or complete, eradication or amelioration of one or more of the physiological symptoms associated with the underlying disorder such that an improvement is observed in the patient, notwithstanding the fact that the patient may still be afflicted with the underlying disorder. For prophylactic benefit, a method of the disclosure may be performed on, or a composition of the invention administered to, a patient at risk of developing cancer, or to a patient reporting one or more of the physiological symptoms of such conditions, even though a diagnosis of the condition may not have been made.

Patient Populations and Cancers

In general, any subject having, or suspected of having, a cancer or other proliferative disorder may be treated using the compositions and methods of the present disclosure. Subjects receiving treatment according to the methods described herein are mammalian subjects, and typically human patients. Other mammals that may be treated according to the present disclosure include companion animals such as dogs and cats, farm animals such as cows, horses, and swine, as well as birds and more exotic animals (e.g., those found in zoos or nature preserves). In a preferred embodiment of the disclosure, a method is provided for the treatment of cancerous tumors, particularly solid tumors. Advantageously, the methods described herein reduces the development of tumors, reduces tumor burden, or produces tumor regression in a mammalian host, and potentiate the effects of anti-cancer drugs. Cancer patients and individuals desiring cancer prophylaxis can be treated with the combinations described herein.

Cancer and tumors generally refer to or describe the physiological condition in mammals that is typically characterized by unregulated cell growth. By means of the pharmaceutical combinations, co-formulations, and combination therapies of the present disclosure, various tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

In one embodiment, the tumor or cancer is chosen from adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangio-carcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Thus, for example, the present disclosure provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

For example, particular leukemias that can be treated with the combinations and methods described herein include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas can also be treated with the combinations and methods described herein. Lymphomas are generally neoplastic transformations of cells that reside primarily in lymphoid tissue. Lymphomas are tumors of the immune system and generally are present as both T cell- and as B cell-associated disease. Among lymphomas, there are two major distinct groups: non-Hodgkin's lymphoma (NHL) and Hodgkin's disease. Bone marrow, lymph nodes, spleen and circulating cells, among others, may be involved. Treatment protocols include removal of bone marrow from the patient and purging it of tumor cells, often using antibodies directed against antigens present on the tumor cell type, followed by storage. The patient is then given a toxic dose of radiation or chemotherapy and the purged bone marrow is then re-infused in order to repopulate the patient's hematopoietic system.

Other hematological malignancies that can be treated with the combinations and methods described herein include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

In one embodiment, the methods and pharmaceutical compositions described herein are used to treat accelerated or metastatic cancers of the bladder, pancreatic cancer, prostate cancer, non-small cell lung cancer, colorectal cancer, and breast cancer.

Pharmaceutical Compositions and Formulations

Another aspect of the present disclosure relates to the pharmaceutical compositions comprising the combinations described herein, together with a pharmaceutically acceptable excipient. The pharmaceutical compositions include the superoxide dismutase mimetics (e.g., those corresponding to Formula (I)), and at least one anti-cancer agent selected from antimetabolite agents, antimitotic agents, and combinations thereof, as discussed above, typically formulated as a pharmaceutical dosage form, optionally in combination with a pharmaceutically acceptable carrier, additive or excipient. In one embodiment, for example, the pharmaceutical composition comprises a superoxide dismutase mimetic, an antimetabolite agent, and a pharmaceutically acceptable excipient. In another embodiment, the pharmaceutical composition comprises a superoxide dismutase mimetic, an antimitotic agent, and a pharmaceutically acceptable excipient. In yet another embodiment, the pharmaceutical composition comprises a superoxide dismutase mimetic, an antimetabolite agent, an antimitotic agent, and a pharmaceutically acceptable excipient. Pharmaceutical compositions according to the present disclosure may be used in the treatment of cancer.

The pharmaceutical compositions described herein are products that result from the mixing or combining of more than one active ingredient and includes both fixed and non-fixed combinations of the active ingredients. Fixed combinations are those in which the active ingredients, e.g., a superoxide dismutase mimetic, antimetabolite, and/or antimitotic compound described herein, are both administered to a patient simultaneously in the form of a single entity or dosage. Non-fixed combinations are those in which the active ingredients, e.g., a superoxide dismutase mimetic, antimetabolite, and/or antimitotic compound described herein, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The above-described superoxide dismutase mimetics, antimetabolites, and/or antimitotics may be dispersed in a pharmaceutically acceptable carrier prior to administration to the mammal; i.e., the components described herein are preferably co-formulated. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route, and in accordance with the conventional route of administration of the component (e.g., the superoxide dismutase mimetic compound, the antimetabolite agent, and/or the antimitotic agent). For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in combination with the compositions of the present disclosure are well known to those of ordinary skill in the art and are selected based upon a number of factors: the particular compound(s) and agent(s) used, and its/their concentration, stability and intended bioavailability; the subject, its age, size and general condition; and the route of administration. Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$ to $C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

In some embodiments, oils or non-aqueous solvents may be employed in the formulations, e.g., to bring one or more of the compounds into solution, due to, for example, the presence of large lipophilic moieties. Alternatively, emulsions, suspensions, or other preparations, for example, liposomal preparations, may be used. With respect to liposomal preparations, for example, any known methods for preparing liposomes may be used. See, for example, Bangham et al., J. Mol. Biol, 23: 238-252 (1965) and Szoka et al., Proc. Natl. Acad. Sci 75: 4194-4198 (1978), incorporated herein by reference. Thus, in one embodiment, one or more of the compounds are administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines. Ligands may also be attached to the liposomes, for instance, to direct these compositions to particular sites of action.

Other pharmaceutically acceptable solvents for use in the pharmaceutical compositions described herein are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), and A. J. Spiegel et al., Use of Nonaqueous Solvents in Parenteral Products, Journal of Pharmaceutical Sciences, Vol. 52, No. 10, pp. 917-927 (1963).

Formulations containing the superoxide dismutase mimetic, antimetabolite agent, and/or antimitotic agent may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions or formulation products employ the superoxide dismutase mimetics, antimetabolite agents, and/or antimitotic agents within the conventionally accepted or standard dosage ranges (discussed above).

In general, particular formulation techniques for superoxide dismutase mimetics, antimetabolite agents, and antimitotic agents are known in the art and/or described in the literature.

For example, formulations for pyrimidine analogs, and in particular gemcitabine, are described in detail in U.S. Pat. No. 5,464,826 (hereby incorporated by reference herein); hard gelatin capsules, tablets, aerosol solutions, capsules, suppositories, suspensions, and intravenous formulations are specifically described.

Various taxane formulations are also known in the art. Some taxane formulations involve, for instance the use of modified fatty acid esters such as polyoxyl 40 hydrogenated castor oil and polyoxyethylated castor oils (e.g., Cremophor EL® solution or Cremophor RH 40® solution) and/or triglyceride-rich oils including for example, Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), and natural or synthetic glycerol derivatives containing the docosahexaenoyl group at levels between 25% and 100% by weight based on the total fatty acid content (e.g., Dhasco® (Martek Biosciences Corp., Columbia, Md.), DHA Maguro® (Daito Enterprises, Los Angeles, Calif.), Soyacal®, and Travemulsion®) Ethanol is a preferred solvent for use in dissolving the taxanes to form solutions, emulsions, and the like.

Formulations for superoxide dismutase mimetics are also known in the art and are generally described, for example, in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041 (each of which is hereby incorporated herein by reference in its entirety).

It is contemplated that co-formulations of the superoxide dismutase mimetic and one or both of the antimetabolite agent and the antimitotic agent may employ conventional formulation techniques for these components individually, or alternative formulation routes, subject to compatibility and efficacy of the various components, in combination.

The above-described pharmaceutical compositions including the superoxide dismutase mimetic, the antimetabolite agent, and the antimitotic agent may additionally include one or more pharmaceutically active components. Suitable pharmaceutically active agents that may be included in the compositions of the present invention include, for instance, antiemetics, anesthetics, antihypertensives, antianxiety agents, anticlotting agents, anticonvulsants, blood glucose-lowering agents, decongestants, antihistamines, antitussives, antineoplastics, beta blockers, anti-inflammatory agents, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's Disease agents, antibiotics, anti-depressants, and antiviral agents. The individual components of such combinations may be administered either sequentially or simultaneously in separate or combined pharmaceutical formulations.

Further Forms of Compounds

With respect to the compounds described herein, for example, the superoxide dismutase mimetics corresponding to Formula (I), the antimetabolite agents, and the antimitotic agents, these compounds may exist in a variety of different forms, each of which and others are contemplated in the instant disclosure.

With regard to stereoisomers, for instance, it should be understood that a solid line designation for the bonds in the superoxide dismutase mimetics corresponding to Formula (I) (and others, such as the particular antimetabolites and antimitotic agents described herein) for attachment of an substituent group to a chiral carbon atom of the compound indicates that these groups may lie either below or above the plane of the page (i.e., ▬R or ⋯⋯R ). All isomeric forms of the compounds disclosed herein are contemplated, including racemates, racemic mixtures, and individual enantiomers, diastereomers, and epimers, as well as appropriate mixtures thereof.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. As noted above, all such isomers, including diastereomers, enantiomers, and mixtures thereof, are considered as part of the compositions described herein.

The methods and formulations described herein may also include the use of N-oxides, crystalline forms (also known as polymorphs), or pharmaceutically acceptable salts of compounds described herein, as well as active metabolites of these compounds having the same or similar type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein (such as the antimetabolite and antimitotic agents) are prepared as prodrugs. A prodrug refers to an agent that is converted into the parent drug in vivo. Prodrugs are often useful because, in some situations, they may be easier to administer than the parent drug. They may, for instance, be bioavailable by oral administration whereas the parent is not, or less so. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound.

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

As noted above, prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol, 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, each of which is hereby incorporated by reference herein in its entirety.

Various forms of prodrugs are well known in the art. For examples of such prodrug derivatives, see: (a) *Design of Prodrugs*, edited by H. Bundgaard, (Elsevier, 1985) and *Methods in Enzymology*, Vol. 42, p. 309-396, edited by K. Widder, et al. (Academic Press, 1985); (b) *A Textbook of Drug Design and Development*, edited by Krosgaard-Larsen and H. Bundgaard, Chapter 5, "Design and Application of Prodrugs," by H. Bundgaard, p. 113-191 (1991); (c) H. Bundgaard, *Advanced Drug Delivery Reviews*, 8, 1-38 (1992); (d) H. Bundgaard, et al., *Journal of Pharmaceutical Sciences*, 77, 285 (1988); (e) N. Kakeya, et al., *Chem. Pharm. Bull.*, 32, 692 (1984); (f) Nogrady, Medicinal Chemistry: A Biochemical Approach, (Oxford University Press, New York (2005)), pages 388-392 (2005); (g) Silverman, The Organic Chemistry of Drug Design and Drug Action, (Academic Press, Inc., San Diego (2004)), pages 352-401; (h) Saulnier et al., Bioorganic and Medicinal Chemistry Letters, Vol. 4, (1994), p. 1985); each of which is hereby incorporated by reference herein in its entirety.

Compounds described herein also include isotopically-labeled compounds, which are identical to those recited in the various compounds, structures, and formulae herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Certain isotopically-labeled compounds described herein, for example those into which radioactive isotopes such as $^{3}H$ and $^{14}C$ are incorporated, may be useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

In additional or further embodiments, the compounds described herein are metabolized upon administration to produce a metabolite that is then used to produce a desired effect, including a desired therapeutic effect.

For the anti-cancer agents described herein (e.g., the antimetabolite and/or antimitotic agents), these compounds may be used in their free base form or may be formed as, and/or used as, pharmaceutically acceptable salts. Types of pharmaceutical acceptable salts, include, but are not limited to: (1) acid addition salts, typically formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g., lithium, sodium, potassium), an alkaline earth ion (e.g., calcium or magnesium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts may generally be recovered by using at least one or more of filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs.

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may also be in various forms, including but not limited to, amorphous forms, milled forms and nano-particulate forms.

Kits/Articles of Manufacture

For use in the therapeutic applications described herein, kits and articles of manufacture are also described. Such kits can include a carrier, package, or container that is compartmentalized to receive one or more containers such as vials, tubes, and the like, each of the container(s) including one of the separate elements to be used in a method described herein (such as, for example, the superoxide dismutase mimetics, antimetabolites, or antimitotics, alone or in combination). Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252 (each of which is hereby incorporated by reference herein). Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. As noted above, a wide array of formulations of the compounds and compositions provided herein are contemplated, as are a variety of treatments for any disease, disorder, or condition that would benefit by treatment with superoxide dismutase mimetics, antimetabolite agents, and/or antimitotic agents, in combination, and with the synergistic effects described herein.

Thus, for example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound (e.g., a superoxide dismutase mimetic) with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use; and package inserts with instructions for use. A set of instructions will also typically be included, which may be a separate sheet or brochure, or may be printed on one or more of the packages, containers, or vials (directly or on a label (such as described below)).

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions or instructions for use of the contents, such as in the methods described herein.

In certain embodiments, the pharmaceutical compositions can be presented in a pack or dispenser device which can contain one or more unit dosage forms containing one or more of the compounds and agents provided herein. The pack can, for example, contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration (FDA) or the European Medicines Agency (EMEA) for prescription drugs, or the approved product insert. Compositions containing one or more compounds provided herein (e.g., the superoxide dismutase mimetic, antimetabolite, and/or antimitotic) formulated in a compatible pharmaceutical carrier can also be prepared, placed in an appropriate container, and labeled for treatment of an indicated condition.

Abbreviations and Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The terms "acetal" and "ketal," as used herein alone or as part of another group, denote the moieties represented by the following formulae, respectively:

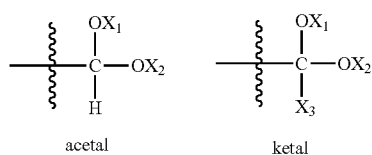

acetal      ketal wherein $X_1$ and $X_2$ are independently hydrocarbyl, substituted hydrocarbyl, heterocyclo, or heteroaryl, and $X_3$ is hydrocarbyl or substituted hydrocarbyl, as defined in connection with such terms, and the wavy lines represent the attachment point of the acetal or ketal moiety to another moiety or compound.

The term "acyl," as used herein alone or as part of another group, denotes the moiety formed by removal of the hydroxyl group from the group—COOH of an organic carboxylic acid, e.g., $X_4C(O)—$, wherein $X_4$ is $X^1$, $X^1O—$, $X^1X^2N—$, or $X^1S—$, $X^1$ is hydrocarbyl, heterosubstituted hydrocarbyl, or heterocyclo, and $X^2$ is hydrogen, hydrocarbyl or substituted hydrocarbyl. Exemplary acyl moieties include acetyl, propionyl, benzoyl, pyridinylcarbonyl, and the like.

The term "acyloxy," as used herein alone or as part of another group, denotes an acyl group as described herein bonded through an oxygen linkage (—O—), e.g., $X_4C(O)$ O— wherein $X_4$ is as defined in connection with the term "acyl."

The term "alicyclic," as used herein alone or as part of another group, refers to a cyclic aliphatic group, wherein the term "aliphatic" takes its normal meaning in the art and includes non-aromatic groups such as alkanes, alkenes and alkynes and substituted derivatives thereof.

The term "alkoxy," as used herein alone or as part of another group, denotes an $—OX_5$ radical, wherein $X_5$ is as defined in connection with the term "alkyl." Exemplary alkoxy moieties include methoxy, ethoxy, propoxy, or 2-propoxy, n-, iso-, or tert-butoxy, and the like. The term "alkoxyaryl" or "alkoxyalkyl" refers to an aryl or alkyl group, respectively, and as defined herein, that is substituted with an alkoxy group.

The term "alkenoxy," as used herein alone or as part of another group, denotes an $—OX_6$ radical, wherein $X_6$ is as defined in connection with the term "alkenyl." Exemplary alkenoxy moieties include ethenoxy, propenoxy, butenoxy, hexenoxy, and the like.

The term "alkynoxy," as used herein alone or as part of another group, denotes an $—OX_7$ radical, wherein $X_7$ is as defined in connection with the term "alkynyl." Exemplary alkynoxy moieties include ethynoxy, propynoxy, butynoxy, hexynoxy, and the like.

The term "alkyl", alone or in combination, means a straight-chain or branched-chain alkyl substituent containing from 1 to about 22 carbon atoms, preferably from about 1 to about 18 carbon atoms, and most preferably from about 1 to about 12 carbon atoms. Examples of such substituents include, but are not limited to, methyl, ethyl, n-propyl, iso-propyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

The term "alkenyl", alone or in combination, means an alkyl substituent having one or more double bonds. Examples of such alkenyl substituents include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl.

The term "alkynyl", alone or in combination, means an alkyl substituent having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl.

The terms "alkylcycloalkyl" and "alkenylcycloalkyl" mean a cycloalkyl substituent as defined herein which is substituted by an alkyl or alkenyl substituent as defined herein. Examples of alkylcycloalkyl and alkenylcycloalkyl substituents include, but are not limited to, 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl.

The terms "alkylcycloalkenyl" and "alkenylcycloalkenyl" means a cycloalkenyl substituent as defined herein which is substituted by an alkyl or alkenyl substituent as defined herein. Examples of alkylcycloalkenyl and alkenylcycloalkenyl substituents include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl.

The amino acid side chain moieties described herein may generally be any moiety attached to the α-carbon of natural or unnatural amino acids, including D and L forms thereof. Thus, for example, the amino acid side chain moiety may correspond to one of the amino acid side chain moieties of the amino acids identified in Table 1.

TABLE 1

| Amino Acid Side Chain Moiety | Amino Acid |
|---|---|
| —H | Glycine |
| —CH₃ | Alanine |
| —CH(CH₃)₂ | Valine |
| —CH₂CH(CH₃)₂ | Leucine |
| —CH(CH₃)CH₂CH₃ | Isoleucine |
| —(CH₂)₄NH₂ | Lysine |
| —(CH₂)₃NHC(=NH)NH₂ | Arginine |
| —CH₂— 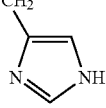 | Histidine |
| —CH₂COOH | Aspartic Acid |
| —CH₂CH₂COOH | Glutamic Acid |
| —CH₂CONH₂ | Aparagine |
| —CH₂CH₂CONH₂ | Glutamine |
| —CH₂— 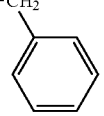 | Phenylalanine |
| —CH₂— 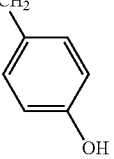 | Tyrosine |
| —CH₂— 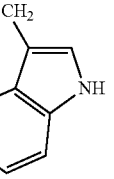 | Tryptophan |
| —CH₂SH | Cysteine |
| —CH₂CH₂SCH₃ | Methionine |
| —CH₂OH | Serine |
| —CH(OH)CH₃ | Threonine |

For convenience purposes, only the unionized form of certain of the amino acid side chain moieties has been shown in Table 1. It is contemplated, however, that the amino acid side chain moieties illustrated in Table 1 may be utilized in the anionic, or conjugate base, form, in combination with a cation, or protonated with a counterion. The amino acid side chain moiety may alternatively be an amino acid side chain moiety of an unnatural amino acid; thus, for example, the amino acid side chain moiety may be selected from alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof.

The terms "amine" or "amino," as used herein alone or as part of another group, represents a group of formula —N($X_8$)($X_9$), wherein $X_8$ and $X_9$ are independently hydrogen, hydrocarbyl, substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring. "Substituted amine," for example, refers to a group of formula —N($X_8$)($X_9$), wherein at least one of $X_8$ and $X_9$ are other than hydrogen. "Unsubstituted amine," for example, refers to a group of formula —N($X_8$)($X_9$), wherein $X_8$ and $X_9$ are both hydrogen.

The terms "amido" or "amide," as used herein alone or as part of another group, represents a group of formula —CON($X_8$)($X_9$), wherein $X_8$ and $X_9$ are as defined in connection with the terms "amine" or "amino." "Substituted amide," for example, refers to a group of formula —CON($X_8$)($X_9$), wherein at least one of $X_8$ and $X_9$ are other than hydrogen. "Unsubstituted amido," for example, refers to a group of formula —CON($X_8$)($X_9$), wherein $X_8$ and $X_9$ are both hydrogen.

The term "aralkyl", alone or in combination, means an alkyl or cycloalkyl substituent as defined herein in which one hydrogen atom is replaced by an aryl substituent as defined herein, such as benzyl, 2-phenylethyl, and the like.

The term "aromatic" refers to a cycloalkylic hydrocarbon ring system having an unsaturated, conjugated π electron system.

The term "aryl", alone or in combination, means a phenyl or naphthyl substituent which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The terms "alkaryl" or "alkylaryl," as used herein alone or as part of another group, denotes an -(arylene)-$X_{11}$ radical, wherein $X_{11}$ is as defined in connection with the term "alkyl."

The term "cyano," as used herein alone or as part of another group, denotes a group of formula —CN.

The term "cycloalkenyl", alone or in combination, means a cycloalkyl substituent having one or more double bonds. Examples of cycloalkenyl substituents include, but are not limited to, cyclopentenyl, cyclohexenyl, cyclooctenyl, cyclopentadienyl, cyclohexadienyl and cyclooctadienyl.

The terms "cyclic", "cycle" or "cycylyl" means a ring structure containing 3 to 20 carbon atoms, preferably 5 to 10 carbon atoms, which may be heterocyclic. The cyclic, cycle or cycylyl can also contain more than one ring.

The term "cycloalkenylalkyl" means an alkyl substituent as defined herein which is substituted by a cycloalkenyl substituent as defined herein. Examples of cycloalkenylalkyl substituents include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl)hexyl, 6-(1-cyclohexen-1-yl)hexyl, 1-(1-cyclopenten-1-yl)nonyl and 1-(1-cyclohexen-1-yl)nonyl.

The term "cycloalkyl", alone or in combination means a cycloalkyl radical containing from 3 to about 10, preferably from 3 to about 8, and most preferably from 3 to about 6, carbon atoms. Examples of such cycloalkyl substituents include, but are not limited to, cyclopropyl, cyclobutyl, cyclopentyl, cyclohexyl, cycloheptyl, cyclooctyl, and perhydronaphthyl.

The term "cycloalkylalkyl" means an alkyl substituent as defined herein which is substituted by a cycloalkyl substituent as defined herein. Examples of cycloalkylalkyl substituents include, but are not limited to, cyclohexylmrthyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl.

The term "cycloalkylcycloalkyl" means a cycloalkyl substituent as defined herein which is substituted by another cycloalkyl substituent as defined herein. Examples of cycloalkylcycloalkyl substituents include, but are not limited to, cyclohexylcyclopentyl and cyclohexylcyclohexyl.

The term "ester," as used herein alone or as part of another group, denotes a group of formula —COO$X_{12}$ wherein $X_{12}$ is alkyl or aryl, each as defined in connection with such term.

The term "ether," as used herein alone or as part of another group, includes compounds or moieties which contain an oxygen atom bonded to two carbon atoms. For example, ether includes "alkoxyalkyl" which refers to an alkyl, alkenyl, or alkynyl group substituted with an alkoxy group.

The term "halide" means chloride, fluoride, iodide, or bromide.

The term "heteroaromatic" or "heteroaryl" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroatom" shall mean atoms other than carbon and hydrogen.

The term "heterocyclic", "heterocycle," "heterocyclo," or "heterocycylyl" means a cyclic, cycle or cycylyl containing at least one other kind of atom, in addition to carbon, in the ring. Such atoms include, but are not limited to, nitrogen, oxygen and sulfur. The heterocyclic can also contain more than one ring. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkanes, alkynes, and alkenes. These moieties also include alkyl, alkenyl, alkynyl, and aryl moieties substituted with other aliphatic or cyclic hydrocarbon groups, such as alkaryl, alkenaryl, alkynaryl, and aralkyl. Unless otherwise indicated, these moieties preferably comprise 1 to 20 carbon atoms.

The term "hydroxy," as used herein alone or as part of another group, denotes a group of formula —OH.

The term "keto," as used herein alone or as part of another group, denotes a double bonded oxygen moiety (i.e., =O).

The term "nitro," as used herein alone or as part of another group, denotes a group of formula $—NO_2$.

The term "nitrogen containing heterocycle" means a ring structure in which 2 carbons and a nitrogen of the ring are shared with the fifteen-membered macrocyclic ligand. The nitrogen containing heterocycle can contain 2 to 20, preferably 4 to 10, carbon atoms, can be substituted or unsubstituted, saturated, partially saturated or unsaturated, and can also contain nitrogen, oxygen and/or sulfur atoms in the portion of the ring which is not also part of the fifteen-membered macrocyclic ligand.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters, ethers, and thioethers.

The term "thioether," as used herein alone or as part of another group, denotes compounds and moieties that contain a sulfur atom bonded to two different carbon or hetero atoms (i.e., —S—), and also includes compounds and moieties containing two sulfur atoms bonded to each other, each of which is also bonded to a carbon or hetero atom (i.e., dithioethers (—S—S—)). Examples of thioethers include, but are not limited to, alkylthioalkyls, alkylthioalkenyls, and alkylthioalkynyls. The term "alkylthioalkyls" includes compounds with an alkyl, alkenyl, or alkynyl group bonded to a sulfur atom that is bonded to an alkyl group. Similarly, the term "alkylthioalkenyls" and alkylthioalkynyls" refer to compounds or moieties where an alkyl, alkenyl, or alkynyl group is bonded to a sulfur atom that is covalently bonded to an alkynyl group.

The term "thiol," as used herein alone or as part of another group, denotes a group of formula —SH.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLE 1

Mouse Colon Tumor Model

A. In a first experiment, fragments of CT26 mouse colon tumor were implanted in female BALB/c mice and allowed to grow for 6 days to a size of about 110 mg (107-115 mg).

On this day, day 6, mice were administered 6 mg/kg of KM4403 or KM4419 intraperitoneally (IP) and dosing was continued twice daily for the duration of the study.

In some groups, gemcitabine was administered on days 6, 9, 12 and 15 at a dosage of 80 mg/kg, also via IP, 10 minutes after the administration of KM4403 or KM4419. The results showed decreased tumor size using combination treatment in comparison to treatment with gemcitabine alone.

B. In a second experiment, fragments of C26 colon tumor were implanted in female BALB/c mice and grown until day 7 at which point they averaged 123 mg.

Groups 1 and 2 (n=8) were given 10 mg/kg or 20 mg/kg of KM4419 twice daily starting at day 7.

In groups 3 and 4 (n=8), gemcitabine was administered at 120 mg/kg or 160 mg/kg IP on days 7, 13 and 16.

In groups 5 and 6 (n=8), both gemcitabine and KM4419 were administered according to the foregoing regimens. Gemcitabine was administered 10 minutes after KM4419 in these groups. The levels of KM4419 were 10 mg/kg and 20 mg/kg, respectively, and the dose of gemcitabine was 120 mg/kg.

As shown in FIG. 1, the combination treatment of gemcitabine with KM4419 at both KM4419 dosage levels decreased the tumor size more effectively than gemcitabine alone and delayed recurrence.

EXAMPLE 2

Non-Small Cell Lung Cancer Tumor Model

Figure 2:
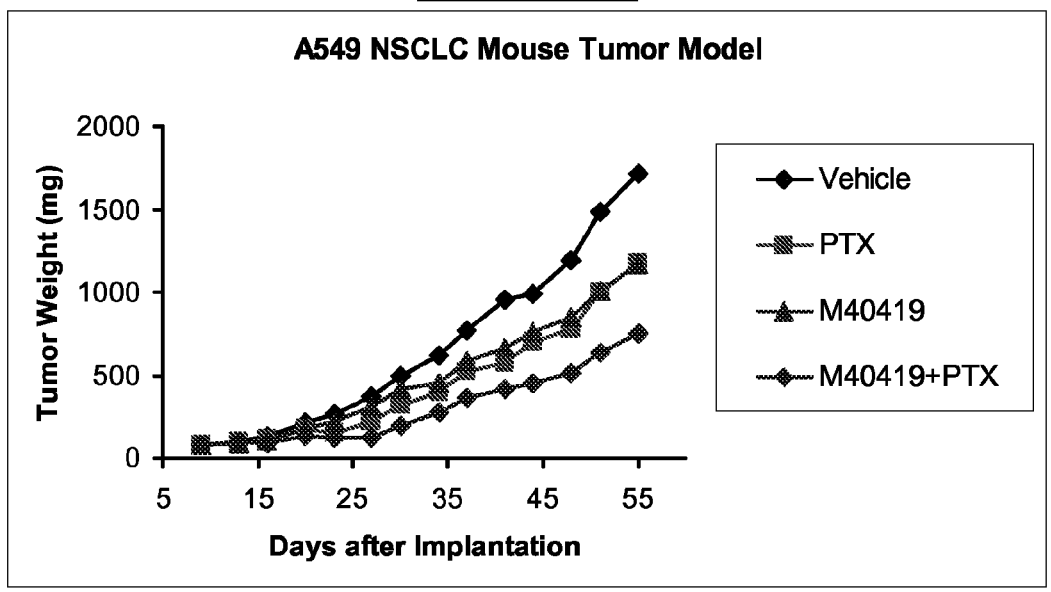
FIG. 2 is a graph that shows the effect of combination of KM4419 with paclitaxel in a mouse model of tumor growth.

In a manner similar to that of Example 1, human A549 non-small lung carcinoma cells were implanted into the flanks of female BALB/c mice, and the tumors were allowed to grow until day 9. Group 1 was administered only vehicle. Group 2 (n=10) was administered only paclitaxel at 12.5 mg/kg IP on days 9 and 13. In group 3 (n=10), the mice were administered 30 mg/kg of KM4419 IP on days 9-23. In group 4 (n=10), a combination of these protocols was administered. The results are shown in FIG. 2 which demonstrate that the combination was more effective than either drug taken alone.

What is claimed is:
1. A method of treating a cancer that is responsive to an antimetabolite or antimitotic anti-cancer agent in a mammalian subject afflicted with the cancer, the method comprising:
   administering to the subject at least one anti-cancer agent selected from antimetabolite anti-cancer agents, antimitotic anti-cancer agents, and combinations thereof, and a selective superoxide dismutase mimetic to potentiate the therapeutic effect of the anti-cancer agent(s); wherein
   the antimetabolite anti-cancer agent is selected from the group consisting of 2-fluorodeoxycytidine, 3'-azido-3'-deoxythymidine, 3'-deoxy-3'-deoxythymidin-2'-ene, 3'-dideoxycytidin-2'-ene, 3-fluoro-3'-deoxythymidine, 5-fluorocytosine, 5-fluorouracil, 5-methylcytosine, 5-propynylcytosine, 5-propynylthymine, 5-propynyluracil, 6-azauridine, 6-mercaptopurine, 8-aza-adenosine, 8-aza-guanosine, 8-fluoro-adenosine, acyclovir, allopurinol, ancitabine, arabinosyl adenine, azacitidine, azathiprine, bromouracil, capecitabine, carmofur, chlorouracil, cladribine, cytarabine, cytosine arabinoside, denopterin, deoxycoformycin, dideoxyuridine, dihydrouracil, doxifluridine, enocitabine, floxuridine, fludarabine, gancylovir, gemcitabine, methotrexate, pemetrexed, pentostatin, pteropterin, raltitrexed, thiamiprine, thioguanine, trimetrexate, salts thereof, and combinations thereof;
   the antimitotic anti-cancer agent is selected from the group consisting of docetaxel, epothilone A, epothilone B, epothilone C, epothilone D, epothilone E, epothilone F, paclitaxel, vinblastine, vincristine, vindesine, vinorelbine, salts thereof, and combinations thereof;

wherein the selective superoxide dismutase mimetic has no significant activity toward hydrogen peroxide and corresponds to Formula (4419):

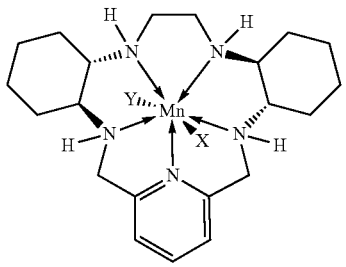

(4419)

wherein X and Y are ligands.

2. The method of claim 1 wherein X and Y are chloro.

3. The method of claim 1 wherein the antimetabolite anti-cancer agent is selected from the group consisting of 5-fluorouracil, capecitabine, 6-mercaptopurine, methotrexate, gemcitabine, cytarabine, fludarabine, pemetrexed, salts thereof, and combinations thereof.

4. The method of claim 1 wherein the anti metabolite anti-cancer agent is selected from the group consisting of capecitabine, 6-mercaptopurine, methotrexate, gemcitabine, cytarabine, fludarabine, pemetrexed, salts thereof, and combinations thereof.

5. The method of claim 1 wherein the antimetabolite anti-cancer agent is a pyrimidine analog other than 5-fluorouracil.

6. The method of claim 1 wherein the antimetabolite anti-cancer agent is gemcitabine or a salt thereof.

7. The method of claim 1 wherein the antimetabolite anti-cancer agent is gemcitabine HCl.

8. The method of claim 1 wherein the anti-cancer agent(s) and the superoxide dismutase mimetic are administered simultaneously.

9. The method of claim 1 wherein the anti-cancer agent(s) and the superoxide dismutase mimetic are administered in sequence.

10. The method of claim 1 wherein the anti-cancer agent(s) is/are administered prior to administration of the superoxide dismutase mimetic.

11. The method of claim 1 wherein the anti-cancer agent(s) is/are administered at least 1 hour, but no more than three days, after administration of the superoxide dismutase mimetic.

12. The method of claim 1 wherein the anti-cancer agent(s) is/are administered within 24 hours after administration of the superoxide dismutase mimetic.

13. The method of claim 1 wherein the superoxide dismutase mimetic is administered within at least 1 plasma half-life of the anti-cancer agent(s), but no more than 4 plasma half-lives of the anti-cancer agent(s).

14. A method of treating a cancer that is responsive to an antimetabolite anti-cancer agent in a mammalian subject afflicted with the cancer, the method comprising:
administering to the subject at least one antimetabolite anti-cancer agent selected from the group consisting of capecitabine, 6-mercaptopurine, methotrexate, gemcitabine, cytarabine, fludarabine, pemetrexed, salts thereof, and combinations thereof, and a selective superoxide dismutase mimetic to potentiate the therapeutic effect of the anti-cancer agent(s); wherein the selective superoxide dismutase mimetic has no significant activity toward hydrogen peroxide and corresponds to Formula (4419):

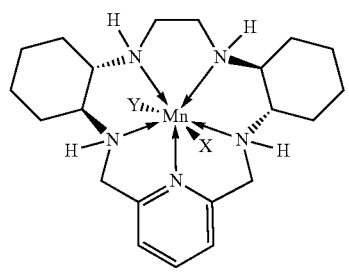

(4419)

wherein X and Y are ligands.

15. The method of claim 14 wherein the antimetabolite anti-cancer agent is gemcitabine or a salt thereof.

16. The method of claim 15 wherein X and Y are chloro.

17. The method of claim 14 wherein the antimetabolite anti-cancer agent is gemcitabine HCl.

18. The method of claim 14 wherein the anti-cancer agent(s) is/are administered prior to administration of the superoxide dismutase mimetic.

19. A method of treating a cancer that is responsive to an antimitotic anti-cancer agent in a mammalian subject afflicted with the cancer, the method comprising:
administering to the subject at least one antimitotic anti-cancer agent selected from the group consisting of docetaxel, paclitaxel, salts thereof, and combinations thereof, and a selective superoxide dismutase mimetic to potentiate the therapeutic effect of the anti-cancer agent(s); wherein the selective superoxide dismutase mimetic has no significant activity toward hydrogen peroxide and corresponds to Formula (4419):

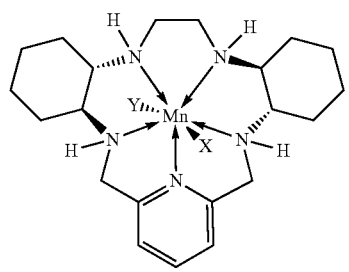

(4419)

wherein X and Y are ligands.

20. The method of claim 19 wherein the antimitotic anti-cancer agent is paclitaxel.

21. The method of claim 20 wherein X and Y are chloro.

22. The method of claim 19 wherein the anti-cancer agent(s) is/are administered prior to administration of the superoxide dismutase mimetic.

* * * * *